United States Patent [19]

Tydeman, deceased et al.

[11] Plant 5,159

[45] Dec. 20, 1983

[54] CHERRY ROOTSTOCK—COB VARIETY

[75] Inventors: Henry M. Tydeman, deceased, late of Maidstone, England, by Elizabeth M. Tydeman, executor; by William M. Tydeman, executor, Bangor, Wales

[73] Assignee: National Seed Development Organisation Limited, Newton, England

[21] Appl. No.: 408,596

[22] Filed: Aug. 16, 1982

[51] Int. Cl.[3] ..... A01H 5/03

[52] U.S. Cl. ..... Plt./37

[58] Field of Search ..... Plt./37

*Primary Examiner*—Robert E. Bagwill

*Attorney, Agent, or Firm*—Burns, Doane, Swecker & Mathis

[57] ABSTRACT

The invention relates to a new and distinct variety of cherry tree useful as a cherry rootstock for supporting ornamental flowering cherry cultivars. The new variety originated as a seedling by crossing *Prunus avium* L. F299/2 and *Prunus pseudocerasus* Lind. It has been found that ornamental cherry cultivars, and in particular Yukon, grow more vigorously on the new variety during the first six years than on *Prunus avium* F12/1 and various inter- and intra-specific hybrids. THe resulting thick trunk formation and the resulting precocious formation of blossoms by the ornamental cherry cultivar are particularly appealing to nurserymen.

5 Drawing Figures

SUMMARY OF THE INVENTION

The original plant was Seedling No. 17 in a family of sterile hybrid seedlings, Fb 2/58, originally produced during 1958 by crossing *Prunus avium* L. F299/2 and *Prunus pseudocerasus* Lind. The Colt dwarfing cherry rootstock (U.S. Plant Pat. No. 4,059) was a member of this same family of seedlings. Following evaluation and testing the new variety of the present invention was found to be useful as an improved cherry rootstock for supporting ornamental flowering cherry cultivars. The pollination, evaluation, and testing were carried out at the East Malling Research Station, Maidstone, Kent, England.

At the present time there is considerable demand for ornamental flowering cherry cultivars. The present variety finds utility as an improved rootstock for use with such ornamental flowering cherry cultivars. More specifically, it has been found that ornamental flowering cherry cultivars such as Yukon grow considerably more vigorously on the rootstock of the present invention particularly during the first six years than on *Prunus avium* F12/1 and various inter- and intra-specific hybrids commonly employed. The increased vigor is manifest in part by a thicker trunk and the more precocious formation of blossoms by the ornamental cherry cultivar. As will be readily recognized by nurserymen, such characteristics are of major economic significance in the horticulture industry.

The cherry rootstock of the present invention has been designated the Cob variety.

Cherry trees of the Cob variety may be easily propagated by hardwood and softwood cuttings. Such asexual reproductions at the East Malling Research Station have demonstrated that the distinctive characteristics are stable and are transmitted without change through succeeding propagations.

BRIEF DESCRIPTION OF THE PHOTOGRAPHS

The accompanying photographs show typical specimens of the improved cherry rootstock of the present invention, while growing during September 1981 at the East Malling Research Station, wherein:

FIG. 1 is a hedge of Cob cherry rootstock planted during 1978 with the height being indicated in centimeters, FIG. 2 is a closer view of a portion of the same hedge shown in FIG. 1, FIG. 3 is a one year old vegetative shoot of the Cob cherry rootstock, FIG. 4 is a leaf of the Cob cherry rootstock with the dimensions being indicated in centimeters, and FIG. 5 illustrates pre-formed root initials appearing at the base of a one year old shoot of the Cob cherry rootstock.

DETAILED DESCRIPTION

Figure 1:
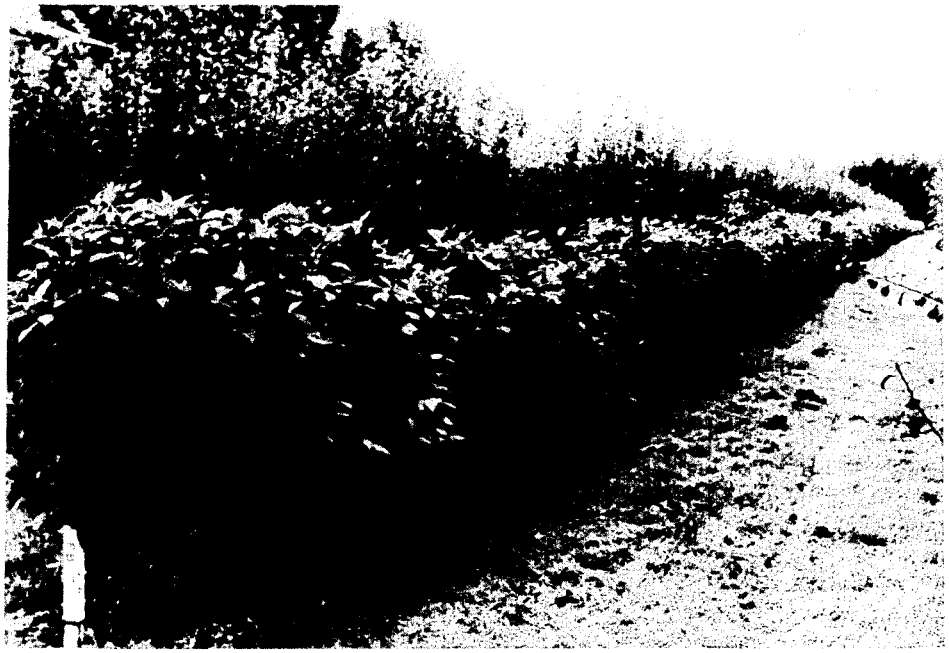
Figure 2:
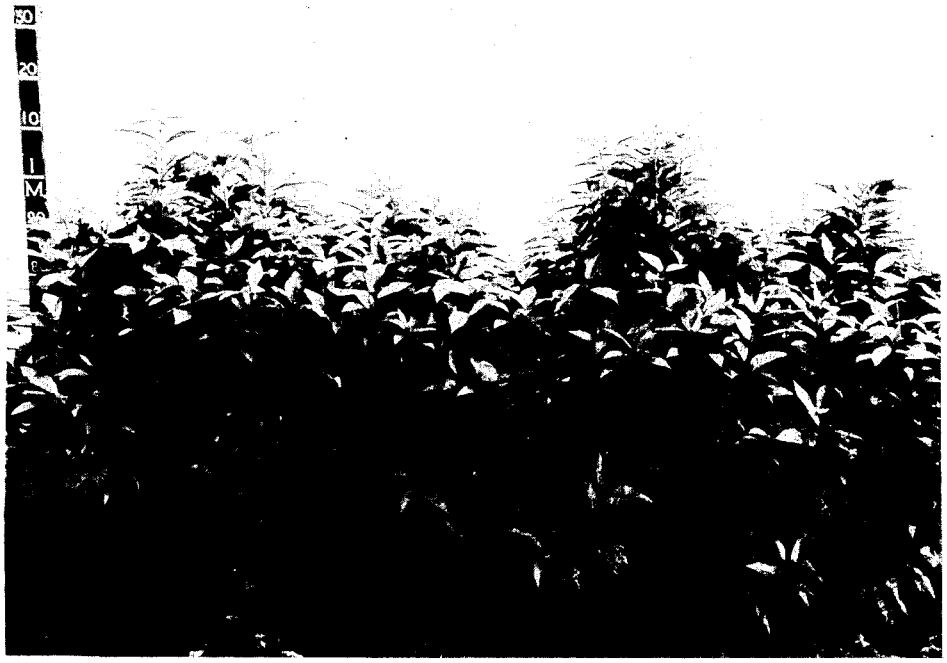
Figure 3:
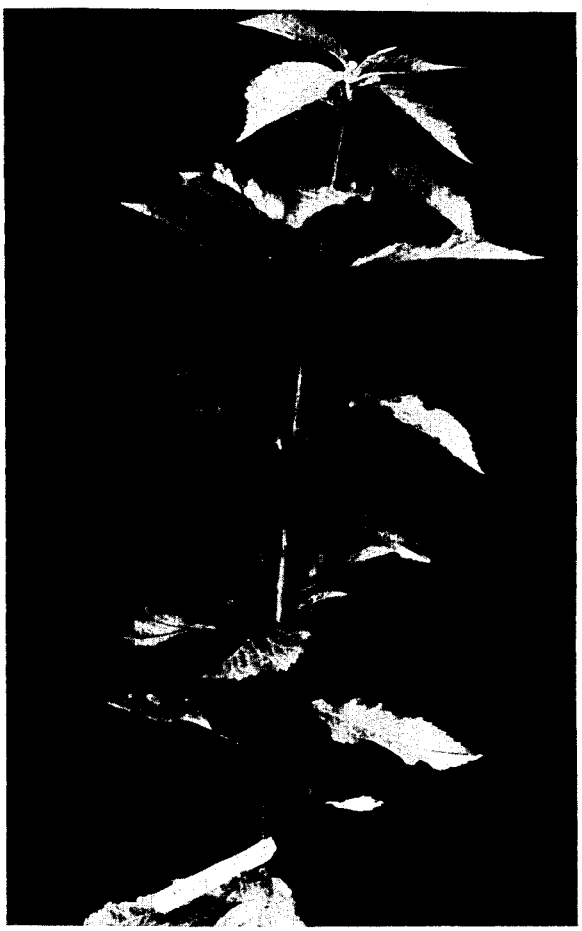
Figure 4:
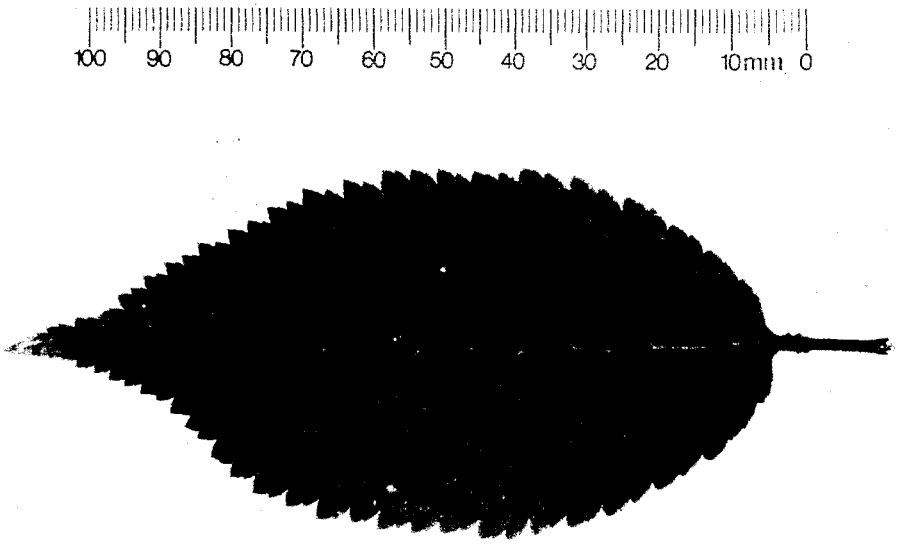
Figure 5:
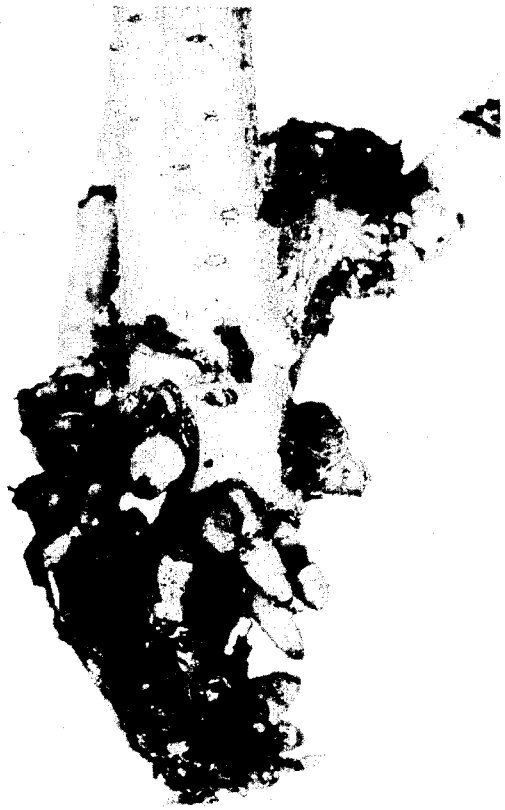

The following is a detailed description of the new cherry rootstock's summer characteristics as observed on one year old shoots produced on hedges in the propagation nursery at the East Malling Research Station, Kent, England.

The colors of the leaves and shoots vary with the growing conditions and generally are not considered to be of value in identifying the rootstock. In those instances where a color assessment has been made reference is to Munsell Color Charts for Plant Tissues, 1st Edition (1952), Munsell Color Co., Inc., Baltimore, Md., U.S.A. In other instances general color terms are used in accordance with their ordinary dictionary significance.

Asexual reproduction of the new Cob variety by hardwood and softwood cuttings, as performed at the East Malling Research Station, shows that the described characteristics and distinctions come true to form and are transmitted through succeeding propagations.

The new variety exhibits erect sturdy shoots up to 80 cm. in length with bright clean green leaves which are slightly upturned with small branched feathery stipules on younger leaf petioles. The tips of the growing shoots are pinkish.

The stems are green with a silvery-white waxy covering on older parts. The lenticels are few and irregularly round in shape. They are whitish in coloration when young and turn to a bright rusty color with age. In hedges which are two years old or more at the end of the growing season, preformed root initials are found on the base of many shoots.

General habit:

*Strength of growth.*—Sturdy shoots of moderate vigor with particularly short internodes.

*Habit of growth.*—Erect, stiff and compact.

*Number of laterals on previous growth.*—Not observed on one-year shoots.

*Feathering on current growth.*—Often feathered, both from base and upper part of shoot.

*Number of shoots on hedge.*—Moderate.

Wood: Summer.

*Color.*—Green when young (Munsell 2.5 GY 6/4), as it matures a silver-white waxy covering develops in places (Munsell 2.5 GY 6/2).

*Hairiness.*—Few short hairs visible with lens. Appears smooth to unaided eye.

*Texture.*—Ridged below leaf attachments, otherwise fairly smooth.

Lenticels:

*Number.*—Not many.

*Conspicuousness.*—Summer conspicuous.

*Shape.*—Roundish to irregular.

*Color.*—Whitish, turning to corky orange brown (Munsell 7.5 YR 6/10).

*Distribution.*—Scattered.

*Size.*—Medium.

Leaves:

*Size.*—Moderately large, length approximately 118 mm., breadth approximately 57 mm.

*Shape.*—Elliptic.

*Base.*—Obtuse, attenuated.

*Apex.*—Acuminate.

*Serrations.*—Doubly serrate.

*Upper surface.*—Flat, shiny, veins sunken with tiny hairs visible under lens.

*Margin.*—Raised slightly, wavy.

*Pose in relation to stem.*—Slightly upturned.

*Color.*—Clear green (Munsell 5 GY 4/6).

*Hairiness on under surface.*—Few hairs on veins visible under lens.

*Texture.*—Upper surface smooth, lower surface rougher.

*Color of tips of shoots.*—Pale and pinkish when actively growing, green when growing has ceased.

Petiole:

*Shape.*—Channelled.

*Length.*—Medium length, approximately 17 mm.

*Color.*—Mainly green with brown-red tinges.

*Pose.*—Upturned.

*Glands.*—One or two, sometimes opposite, at or just below leaf junction.

Stipules (not always present):

*Size.*—Moderate, branched.

*Margin.*—Parted.

*Shape.*—Feathery.

*Pose.*—Erect.

Buds:

*Size.*—Small.

*Shape.*—Pear shaped.

*Compactness.*—Neat, bud scales overlapping.

*Color.*—When young green with pink tinges to edge of bud scales. Older, a brownish-red color.

*Hairiness.*—Not hairy.

*Pose.*—Almost upright, but separate from shoot.

*Base.*—Very slightly extended.

General characteristics:

*Suckering.*—Low.

*Yield potential.*—Not applicable for ornamental cultivars.

*Compatibility.*—Tests to date indicate no problems.

*Stem girth.*—Rapid increase in girth which is an important criterion for ornamental trees.

*Blossom potential.*—Rapid early shoot growth produces a large blossom bearing surface.

I claim:

1. A new and distinct variety of cherry tree useful as an improved rootstock for ornamental flowering cherry cultivars, substantially as illustrated and described, which when used as such rootstock facilitates more vigorous growth, enhanced blossom formation, and thicker trunk growth during the first six years.

* * * * *